US008609084B2

(12) United States Patent
Pujos

(10) Patent No.: US 8,609,084 B2
(45) Date of Patent: Dec. 17, 2013

(54) PROTECTION OF PLANTS AGAINST THEIR PATHOGENIC AGENTS

(75) Inventor: Philippe Pujos, Lille (FR)

(73) Assignee: Lesaffre et Compagnie, Paris (FR)

( * ) Notice: Subject to any disclaimer, the term of this patent is extended or adjusted under 35 U.S.C. 154(b) by 748 days.

(21) Appl. No.: 12/158,116

(22) PCT Filed: Dec. 21, 2006

(86) PCT No.: PCT/FR2006/051414
§ 371 (c)(1),
(2), (4) Date: Jun. 19, 2008

(87) PCT Pub. No.: WO2007/074303
PCT Pub. Date: Jul. 5, 2007

(65) Prior Publication Data
US 2009/0010905 A1      Jan. 8, 2009

(30) Foreign Application Priority Data

Dec. 21, 2005   (FR) ..................... 05 13050

(51) Int. Cl.
*A01N 63/00*            (2006.01)
(52) U.S. Cl.
USPC ........................ 424/93.51; 504/117
(58) Field of Classification Search
None
See application file for complete search history.

(56) References Cited

U.S. PATENT DOCUMENTS

| 5,518,987 | A * | 5/1996 | Winston ................ 504/101 |
| 2005/0271629 | A1 | 12/2005 | Paul | |

FOREIGN PATENT DOCUMENTS

| EP | 1 815 742 A1 | 8/2007 |
| EP | 1 949 789 A1 | 7/2008 |
| JP | 2005-73640 A | 3/2005 |
| WO | 99/03346 A1 | 1/1999 |
| WO | 02/091824 A2 | 11/2002 |
| WO | 2004/002227 A1 | 1/2004 |
| WO | 2005/070213 A2 | 8/2005 |
| WO | 2005/113128 A1 | 12/2005 |
| WO | 2006/049201 A1 | 5/2006 |

OTHER PUBLICATIONS

Albersheim et al., Journal of Supramolecular Structure, 1977, vol. 6, p. 599-616.*
Reuveni et al., Plant Disease, 2003, vol. 87, No. 8, p. 933-936.*
Smith et al., Journal of Dairy Research, 1975, vol. 42, No. 1, 123-138.*
El-Ghaouth et al., Plant disease, 2000, vol. 84, No. 3, p. 243-248.*
Examination Report dated Apr. 28, 2010, New Zealand Patent Application No. 569592.
O. L. Ozeretskovskaya, et al., "Oligosaccharins as Regulatory Molecules of Plants", Russian Journal of Plant Physiology, 1996, pp. 648-655, vol. 43, No. 5.
T. H. Nguyen, et al., "Composition of the cell walls of several yeast species", Applied Microbiology and Biotechnology, Aug. 1998, pp. 206-212, vol. 50, No. 2.
Louis Pillemer, et al., "The Properdin System and Immunity III the Zymosan Assay of Properdin", J. Exp. Med., 1957, pp. 1-13, vol. 103, No. 1.
J. W. Buck, "Combinations of Fungicides with Phylloplane Yeasts for Improved Control of Botrytis cinerea on Geranium Seedlings", Phytopathology, 2004, pp. 196-202, vol. 94, No. 2.
Abstract for Application No. FI 2009/051017, published Jun. 24, 2010, partial claims only in English.
Ayers, Arthur R, et al., "Host-Pathogen Interactions, XI. Composition and Structure of Wall-Released Elicitor Fractions", vol. 57, Plant Physiol. (1976), pp. 766-774.
Eurasyp webpage: http://www.eurasyp.org/public.divres.faq.showfaqs.screen, Jul. 30, 2011.
Google Search on: glucans, mannan, alcalin, yeast, Jul. 30, 2011.
Hahn, Michael G., et al., "Host-Pathogen Interactions, XIV. Isolation and Partial Characterization of an Elicitor From Yeast Extract"; vol. 62, Plant Physiol., (1978) pp. 107-111.
Yamamoto, Hirobumi, et al., "Stimulation of prenylated flavanone production by mannans and acidic polysaccharides in callus culture of *Sophora flavescens*", vol. 40, Issue 1, Sep. 1995, pp. 77-81 (Abstract only).
Oommen, Abraham, et al., "The Elicitor-Inducible Alfalfa Isoflavone Reductase Promoter Confers Different Patterns of Developmental Expression in Homologous and Heterologous Transgenic Plants", The Plant Cell, vol. 6, (1994), pp. 1789-1803.
Reglinski, T., et al., "Induction of resistance mechanisms in barley by yeast-derived elicitors", Ann. appl. Biol. (1994), 124, pp. 509-517.
Broeckling, Corey D., "Metabolic profiling of Medicago truncatula cell cultures reveals the effects of biotic and abiotc elicitors on metabolism", Journal of Experimental Botany, vol. 56, No. 410, (2005), pp. 323-336.

* cited by examiner

*Primary Examiner* — Kade Ariani
(74) *Attorney, Agent, or Firm* — Sughrue Mion, PLLC

(57) ABSTRACT

This invention relates compositions and methods for protecting plants against various pathogenic agents such as fungi, viruses and bacteria. The invention can be used alone or in alternation and/or in combination with other plant protection means, and is suitable for the treatment of multiple plant species.

27 Claims, No Drawings

PROTECTION OF PLANTS AGAINST THEIR PATHOGENIC AGENTS

CROSS REFERENCE TO RELATED APPLICATIONS

This application is a National Stage of International Application No. PCT/FR2006/051414 filed on Dec. 21, 2006, claiming priority based on French Patent Application No. 05 13050, filed Dec. 21, 2005, the contents of all of which are incorporated herein by reference in their entirety.

This invention relates to compositions and methods for protecting plants against various pathogenic agents such as fungi, viruses and bacteria. The invention can be used alone or in alternation and/or in combination with other plant protection means, and is suitable for the treatment of multiple plant species.

Among the pathogenic agents, fungi, which are responsible for fungal or cryptogamic diseases, have the biggest economic impact. Each plant species is susceptible to one or more main diseases, which are able to strongly reduce their vitality, growth and ultimately the quantity and/or quality of the crop.

Various parameters effect the disease development, such as the soil conditions and fertilisation, varietal susceptibility, the growing system (preceding crops, cultivation, number of plants or seedlings per hectare, pruning system, etc.), and especially climatic conditions. But acting upon some of these parameters is generally not enough to sufficiently limit damages caused by diseases. So, to avoid these damages, optimise and secure the yield, the farmers treat the crops at appropriate time with a crop protection product, often protective ones. More often than not, the used products are chemicals. Most of them are very effective, but can result in health risks for the people who use them, and leave residues on the treated products, in the soil and in the draining water. Furthermore, the repeated use of certain fungicides acting on the same metabolic site makes strains becoming resistant to these fungicides.

To counteract this, it is necessary to limit the number of treatments per year with agrochemical products of the same family, alternate chemical families with different modes of action, and to use all other means unfavourable to the pathogenic agent.

In this situation, there is a real and important need for alternative solutions against plant diseases. Ideally, these solutions should act in a different way to existing chemical fungicides, not leave chemical residues on the produces and in environment and be safer and healthier for the people who use it. Such treatments could be used alone or in alternation, and/or in combination with current chemical treatments or all other treatments, to prevent the occurrence and limit the development of these pathogens, and of their resistant strains, on plants, and limit the risk to the human and the environment.

SUMMARY OF THE INVENTION

This invention provides new compositions and methods for the treatment or the protection of plants against pathogenic agents. In particular, the invention involves proving that, unexpectedly, yeast cell walls have the capacity to efficiently protect plants against infection by pathogenic agents. This effect is obtained through simply contacting plants with cell walls, through spraying for example.

The obtained results show that the treatment of plants with yeast cell walls provides protection not only to the treated organs or treated parts of the plant (direct action at the contact point), but also to any organs appearing later. The cell walls cannot penetrate inside the plant to be transported by the sap, therefore it is not a systemic action. Meanwhile, such a result suggests the inducement of immune defense mechanisms of the plant, and therefore allows us to envisage a long period of protection, of one month or more, and a multi-purpose action of the compositions and methods of the invention.

Therefore, one embodiment of the invention involves the use of yeast cell walls, or a composition comprising yeast cell walls, for treating or protecting plants against diseases produced or caused by pathogenic agents, in particular fungi, bacteria or viruses.

Another embodiment of the invention involves the use of yeast cell walls, or a composition comprising yeast cell walls, to induce or stimulate the plants' immune defenses against pathogenic agents.

The invention also relates to a method for treating or protecting plants against diseases produced or caused by pathogenic agents, in particular fungi, bacteria or viruses, comprising applying yeast cell walls or a composition comprising yeast cell walls to the plant or to a part thereof.

A further embodiment of the invention is a process to induce or stimulate the immune defense mechanisms of a plant (against pathogenic agents), consisting of applying yeast cell walls or a composition comprising yeast cell walls, to the plant or to a part thereof.

As it will further be described in the following text, the invention can be applied to all types of plant, in particular to graminaceae and dicotyledons, to annual, biennial and perennial plants, to vegetables, to cereals including wheat, barley and rice, to corn, sorghum, millet, oil seed crops, protein crop, to potatoes, beets, sugar cane, tobacco, to ligneous plants, to trees (fruit-trees or not), to vines, ornamental plants, etc. Moreover, pathogenic agent can be of various types, such as a fungus, bacteria, virus, mycoplasm, spiroplasm or a viroid.

The yeast cell walls used in the invention can derived from any species of yeast, in particular *Saccharomyces* genus, in particular *S. cerevisiae* and can be obtained or prepared according to techniques known by the one skilled in the art, which will be described in the following text, in particular autolysis, separation, concentration, etc.

A further embodiment of the invention relates to a (phytopharmaceutical) composition comprising yeast cell walls, which can be administered or applied on a plant or contacting with it or only with any specific organ thereof, in particular the leaves, flowers, fruits, stem, trunk or roots. Such a composition can be described as phytopharmaceutical product.

Said composition can be in the form of a concentrated or not liquid, a wettable or not powder, dispersible or other pellets, or all other forms adapted to the application of yeast cell walls to organ(s) of the plant targeted by the treatment, for example, spraying after dilution, suspension or others, in water or another carrier, on the aerial parts of the plant, in the soil or by feeding solution, at the roots of the plant, etc.

Preferably, the compositions of the invention can further comprise formulation, dispersing, stabilising, surfactant agents, etc.

Another object of the invention relates to a (phytopharmaceutical) composition comprising yeast cell walls in combination with a fungicidal, antiviral or antibacterial agent, so they can be applied simultaneously, separately or at a different time.

The invention also relates to a method to fight against disease caused by pathogenic agents in plants, including the application of yeast cell walls, or a composition comprising yeast cell walls, optionally in alternation or in combination with another active treatment against said pathogenic agent.

The invention also relates to a method to prevent or limit the development of pathogens resistant to a specific group of active substances, wherein the plant is treated with yeast cell walls or a composition comprising yeast cell walls in order to reduce the selection pressure of resistant strains to said group of active substances; or wherein the treatment(s) of the plant with a substance from said group of active substances is(are) alternated or combined with treatment(s) of the said plant with yeast cell walls or a composition comprising yeast cell walls.

The invention also relates to the use of a composition comprising yeast cell walls to increase the global efficiency of the phytosanitary protection, by reducing the level of infection and/or limiting the release of the inoculum.

The invention also aims to use a composition comprising yeast cell walls to obtain long term, partial or complete, phytosanitary protection, for example of at least a month and a half.

The invention also concerns a method to limit the quantity of residues from agrochemical products in or on the consumable produce, in the soil and in the water during treatment of crop or a plant. The method includes treatment(s) of said crop or plant with yeast cell walls or a composition comprising yeast cell walls.

The invention also relates to the use of yeast cell walls or a composition comprising yeast cell walls to prevent or treat diseases in organic or ecological farming.

DETAILED DESCRIPTION OF THE INVENTION

As previously described, the invention relates to a method and products to fight against pathogenic agents in plants, as prevention or as a cure. In particular, the invention depends on the proving of advantageous and unexpected properties of yeast cell walls, and proposes their use in the fight against plant diseases caused by pathogenic agents.

This invention in particular is based on the discovery that yeast cell walls are capable of protecting the organs or parts of the plant treated directly with the compositions of the invention (i.e., they act directly at the contact site), and also the organs or parts of the plant appearing after treatment. The cell walls cannot penetrate the plant to be transported by the sap, it is not a systemic action. However, the protection diffusion to the whole plant and to newly formed organs suggests an induction or stimulation of the immune defense mechanisms, such as those already known, using b-aminobutyric acid, 2,6-dichloroisonicotinic acid, acibenzolar-s-methyl, or some algae extracts (patents or patent applications FR2,868,253; WO03/092384; WO97/14310 and WO99/53761) and allows contemplation of a long period of protection, of one month or more, and the multi-purpose action of the compositions of the invention.

Furthermore, according to the invention, the yeast cell walls are less likely to cause resistance because they have no direct effect on the pathogenic agents.

The results disclosed in the invention are particularly surprising, because they show that it is not necessary to use purified molecules, but that the whole yeast cell walls are active without their components being previously isolated or separated. Furthermore, there is no need of further chemical modifications of the yeast cell walls.

Therefore, the invention relates to the use of yeast cell walls or a composition comprising yeast cell walls for the protection of plants against disease caused by pathogenic agents.

The invention also concerns the use of yeast cell walls or a composition comprising yeast cell walls to induce or stimulate the plant's immune defense mechanisms against pathogenic agents.

The invention also concerns a method to induce or stimulate the plant's immune defenses against a pathogenic agent, including the application to the plant, or to part thereof of yeast cell walls or a composition comprising yeast cell walls.

The yeast cell walls used in this invention can be produced from different species of yeast or possibly a mix thereof. Baker's yeast is preferred. Baker's yeast is a yeast belonging to the *Saccharomyces* genus, essentially produced by multiplication or aerobic growth as disclosed in chapter 6 《Baker's yeast production》 from the reference book 《Yeast technology》. The yeast can also be brewer's yeast, oenological yeast or distillery yeast. Other types of yeast can be used in the context of this invention, for example yeast genus from the *Kluyveromyces* spp, *Pichia* spp, *Metschnikowia* spp and *Candida* spp groups.

Yeast is a cell schematically composed of an envelope and content. The envelope is called the 《cell wall》.

The industrial products called yeast 《cell walls》 can be produced in different ways, from different types of yeast, optionally as a mix, with techniques known in the art. In a particular embodiment of the method, the yeast cell walls can be produced by the lysis (autolysis or heterolysis) of yeast cells, for example *Saccharomyces cerevisiae*, followed by the separation of the soluble and insoluble fractions, for example, by physical means such as centrifugation, and then collecting the insoluble fraction. In this way, the insoluble fraction is typically collected by removing the soluble fraction by centrifugation. The insoluble fraction is called the 《yeast cell walls》. The resulting soluble fraction is clear in colour and of weak turbidity and is called 《yeast extract》.

The autolysis of yeast is the hydrolysis of the cellular content of the yeast by its own enzymes. It is typically achieved by suspending the yeast in certain physical medium conditions and/or in contact with activators resulting in the death of the yeast and the liberation of its enzymes into the cellular body. The hydrolysis of the cellular content produces soluble compounds. This separated and collected soluble fraction constitutes 《yeast extract》. The insoluble fraction collected from said separation step constitutes the product known as "yeast cell walls". This product includes the cytoskeleton of yeast, and the non-solubilized membranes and components by autolysis or heterolysis. The insoluble fraction is generally collected through the aqueous suspension of the yeast cell walls, the dry matter content thereof being typically 10 to 15% (weight/volume). The cell walls correspond to about 25 to 45% of dry weight of the entire yeast cell, an average of about of 35%.

Cell walls can be further submitted to chemical treatment such as extraction or functionalisation, for example a delipidation. In a preferred embodiment of the invention, unmodified yeast cell walls can be used, in particular not submitted to such treatments.

In this invention, yeast cell walls or any composition comprising yeast cell walls, from the same type of yeast or from different types or species thereof, can be used.

Such products are also commercially available, in particular Springcell 8001 0 PW from Biospringer SA (F-94 Maisons-Alfort) or Pronady from Prodesa (Bra. Valinhos).

In the invention, all products comprising yeast cell walls, with varying degrees of dehydration, can be used as raw matter. In a preferred embodiment, an aqueous suspension of the yeast cell walls is used, preferably at a concentration of less than 20% dry matter content, more preferably less than 17% or even 14%. In another preferred embodiment, products derived from drying of a liquid suspension, for example by atomisation, and comprising more than 80% dry matter content, preferably more than 85, 90, 93 or 95%, are used.

In a particular embodiment of the invention, phytosanitary (or phytopharmaceutical) compositions (or preparations) can be prepared, with more or less concentrated, so as to be mixed with a liquid or solid carrier for their application, comprising yeast cell walls as an active ingredient, as defined above. Professional farming often uses concentrated phytosanitary products which are diluted with water for spraying, or mixed with a fertiliser or an improvement for made-up soil. In a particular embodiment, the composition of the invention is therefore a concentrated phytosanitary composition, in dry or liquid formulation.

In another particular embodiment of the invention, ready-to-use compositions are prepared, optionally in a liquid or solid form. In a ready-to-use preparation, the active ingredient (comprising yeast cell walls) is already mixed with a suitable carrier for use on plants, for example, a liquid to fill a sprayer, a fertiliser, an underground growing substrate, etc.

Such products or compositions can include any adapted formulation agent in addition to the active ingredient.

Thus, a particular embodiment of the invention relates to all compositions, especially phytopharmaceutical or phytosanitary one, comprising yeast cell walls.

According a first embodiment, the composition is a dry composition, for example powder or granules.

In another embodiment, the composition is a liquid composition, preferably an aqueous liquid. It could particularly be a suspension, gel, cream, paste, etc.

In a preferred embodiment, the compositions further contain one or more formulation agents. Generally, the compositions according to the invention contain approximately from 0.1% to 99.9% (in weight) of the active ingredient and one or more solid or liquid formulation agent(s).

Formulation agent(s) can comprised of any compound or any inert matter allowing the transport or to facilitate or optimise it, the storage, the manipulation and/or the application of the active ingredient to the plant or a part thereof. Such agents are suitable to the aims of the invention: conservation of active agents, agents for maintaining in suspension the cell walls or other active substances during storage or during the use in the preparation of treatment drench, anti-moss agents, anti-dust agents, adhesion agents to the plant, and others. This or these agent(s) can be solid or liquid, and used alone or mixed.

Formulation agent(s), and in particular those suitable to spraying, can be selected from surfactant agents, dispersants, preservatives, wetting agents, emulsifiers, adhesion agents, buffering agent etc., and can be used alone or mixed.

In a particular embodiment, the composition further includes another active agent, preferably a fungicidal, antibacterial or antiviral agent. The fungicidal agent can be chosen, for example, from organic agrochemical fungicides or inorganic mineral fungicides based on sulphur and/or copper.

Examples of organic agrochemical fungicides currently available are in particular chloronitriles, including chlorothalonil, carbamates, including dithiocarbamates such as mancozeb, phtalimides, including captan, sulphonamides, guanidines, quinones, quinolines, thiadiazines, anilides, hydroxyanilides, and phenylamides, imidazolinones, oxazolidinediones, strobilurines, cyanoimidazoles, fluazinam, dinocap, silthiofam, dicarboximides, fludioxonil, organophosphorus, propamocarb HCl, diphenylamine, pyridylamines, sterol biosynthesis inhibitors (SBI) including imidazoles, pyrimidines, hydroxypyrimidines, anilinopyrimidines, triazoles, spiroxamine, morpholines and piperidines, fenhexamid, hymexazol, zoxamide, diethofencarb, benzimidazoles, pencycuron, quinoxyfen, iprovalicarb, cymoxanil, dimethomorph, phosphonates, triazines, etc.

The invention can also be used in alternation, in association or combination with one or more components which act as elicitors of plant defense for example b-aminobutyric acid, 2,6-dichloroisonicotinic acid, acibenzolar-s-methyl, or some algae extracts (patents or patent applications FR2,868,253; WO03/092384; WO97/14310 and WO99/53761). Examples of such compounds are in particular laminarine and ulvans.

The products or compositions of the invention can be applied in different ways and according to different treatment protocols or programmes.

According to a preferred embodiment, the products or compositions are applied by spraying, in particular of leaves or soil pulverisation.

Alternatively, the products or compositions can be applied as a mixture with fertiliser, cultivation support, the watering or others. The composition can also be administered to the roots by spraying the soil, mechanical incorporation, as a mixture with the fertiliser, soil improvement, in pre-mix or others.

Thus, the invention relates to any composition, in particular phytopharmaceutical (or phytosanitary) or ready-to-use, comprising yeast cell walls as an active ingredient. Such compositions comprise advantageously one or more excipients suitable for application on plants, for example in spray or powder form, in particular for domestic or gardening use. Such compositions can further comprise one or more additional active agents, for example fungicidal, antibacterial, antiviral agents or one or several fertilisers, for their simultaneously, separately, or sequentially application on the plant. Other ready-to-use compositions, for example, mixed with fertiliser for soil intake or a cultivation support can be used.

Products or compositions of the invention can be applied on the whole plant or only on one or more parts thereof, for example, the leaves, the stems, the flowers, the trunk and/or the roots. They can also be used on the plant propagation materials, for example seedling, seeds, or the plants, in crod or not. Due to their mode of action, the products of the invention should protect efficiently plants against pathogenic agents for a significant period of time, possibly for more than one month. Repeated application can be contemplated by the user at chosen intervals.

The quantity applied is defined by the man of the art, in particular depending on the pathogenic agent being treated, the type of plant, the combinations used, etc. The quantity applied is preferably sufficient to protect the plant against pathogenic agents, or to limit or stop the development and the effects of this pathogenic agent. This quantity can be determined by testing in field for example.

According to the invention, the composition is applied or used in an efficient dose of more than 1 mg/l of yeast cell walls when the product is used for spraying up to the point of run-off, or more than 1 g/ha when spraying with a small amount of water. Preferably, the efficient dose is from 1 to 1000 mg/l of yeast cell walls when the product is used for spraying up to the point of run-off, or again from 1 to 1000 g/ha in other cases.

In a particular embodiment, the composition is applied or used in an efficient dose from 1 to 250 mg/l of yeast cell walls, preferably from 2.5 mg to 25 mg/l, when the product is used to spray up to the point of run-off or again from 1 to 250 g/ha, preferably between 2.5 and 25 g/ha in other cases, for example when spraying with a small amount of water. Independently of the dosage used, the composition can be produced, transported and/or sold in various concentrations. In this way, when the product is in a dry form, for example, it can contain 96% of yeast cell walls in weight. A liquid product can be in suspended form comprising, for example, 13% yeast cell walls in dry material. The product can also be ready-to-use, i.e., comprising yeast cell walls at a concentration of around 25 mg/l. The concentration of active matter in the products of the invention or during their application can be adapted by the man skilled in the art, and higher doses than those described above can be used.

Furthermore, as previously described, the products and compositions of the invention can be used in alternation and/or in combination with one or more other treatments.

The present invention also involves a method of fighting against disease caused by fungi in plants, including applying yeast cell walls, or a composition comprising yeast cell walls, to the plant in alternation or in combination with an antifungal treatment.

One particular embodiment of the invention involves the method of fighting against diseases caused by bacteria in plants, including the application on the plant of yeast cell walls, or a composition comprising yeast cell walls, in alternation or in combination with an antibacterial treatment.

Another particular embodiment of the invention involves a method for preventing and limiting the development of resistant fungi strains to a family of fungicide agents, wherein the plant is treated by yeast cell walls, or a composition comprising yeast cell walls for reducing the selection pressure of the strains resistant to said family of fungicide agents, or wherein the treatment(s) of the plant with a substance from said family of fungicide agents is (are) alternated or combined with the treatment(s) of said plant using yeast cell walls, or a composition comprising yeast cell walls.

Another embodiment of the invention involves a method for preventing or limiting the development of resistant bacteria strains to a family of antibacterial agents, wherein the plant is treated with yeast cell walls, or a composition comprising yeast cell walls for reducing the selection pressure of the strains resistant to said family of antibacterial agents, or where the treatment(s) of the plant with a substance from said family of antibacterial agents is (are) used in alternation or in combination with the treatment(s) of said plant by yeast cell walls, or a composition comprising yeast cell walls.

The invention can be applied for any plant, in an open field, orchard, forest, greenhouse or indoor or garden plants. The invention can also be applied to graminaceae and dicotyledons, to annual, biennial and perennial plants, to vegetables, to cereals including wheat, barley and rice, to corn, sorghum, millet, oil seed, protein crop, to potatoes, beets, sugar cane, tobacco, ligneous plants, trees, fruit-trees or not, to vines, ornamental plants, etc.

According to a first particular embodiment, the plant is a fruit-tree, for example, a pome fruit-tree in particular selected from apple-trees, pear-trees and citrus-trees.

In another particular embodiment, the plant is chosen from the vine, cereals, in particular wheat, canola, beet, potato, beans, tomato, cucumber, lettuce or strawberry.

The invention is not limited to any particular type of plant; it can be used on all plants.

The method of the invention can be used to fight against all types of pathogenic agents, and in particular fungi, viruses, bacteria, mycoplasms, spiroplasms or viroids. A few specific examples of pathogenic agents are the fungi of the *Alternaria* spp genus, for example *A. solani*, *Ascochyta* spp for example *A. fabae* or *A. pinodella*, *Botrytis* spp for example *B. cinerea*, *Bremia* spp, for example *B. lactucae*, *Cercospora* spp, for example *C. beticola*, *Cladosporium* spp, for example *C. allii-cepae*, *Colletotrichum* spp, for example *C. graminicola*, *Erysiphe* spp, for example *E. graminis*, *Fusarium* spp, for example *F. oxysporum* and *F. roseum*, *Gloeosporium* spp, for example *G. fructigenum*, *Guignardia* spp, for example *G. bidwellii*, *Helminthosporium* spp, for example *H. tritici-repentis*, *Marssonina* spp, for example *M. rosae*, *Monilia* spp, for example *M. fructigena*, *Mycosphaerella* spp, for example *M. brassicicola*, *Penicilium* spp, for example *P. expansum* or *P. digitatum*, *Peronospora* spp, for example *P. parasitica*, *Pezicula* spp, *Phragmidium* spp, for example *P. rubi-idaei*, *Phytophtora* spp including *P. infestans*, *Plasmopara* spp including *P. viticola*, *Podosphaera* spp, for example *P. leucotricha*, *Pseudocercosporella* spp including *P. brassicae*, *Pseudoperonospora* spp, for example *P. cubensis*, *Pseudopeziza* spp, for example *P. medicaginis*, *Puccinia* spp *P. graminis*, *Pythium* spp, *Ramularia* spp including *R betae*, *Rhizoctonia* spp, for example *R. solani*, *Rhizopus* spp, for example *R. nigricans*, *Rynchosporium* spp, such as *R. secalis*, *Sclerotinia* spp or such as *S sclerotiorum*, *Septoria* spp, for example *S. nodorum* or *S. tritici*, *Sphaerotheca* spp such as *S. macularis*, *Taphrina* spp, for example *T pruni*, *Uncinula* spp, for example *U. necator*, *Ustilago* spp, for example *U. tritici* and *Venturia* spp, for example *V. inaequalis*.

The specific pathogenic agent, responsible for apple-tree scabs, is *Venturia inaequalis*.

Examples of bacteria which affect crop particularly include the species *Corynebacterium*, *Clavibacter*, *Curtobacterium*, *Streptomyces*, *Pseudomonas*, *Xanthomonas*, *Erwinia* spp and genus and particularly *E. amylovora*, *E. carotovora*, *E. chrysanthemi*. Examples of viruses infecting crop are for example the tobacco mosaic virus or the potato Y virus.

In one particular embodiment of the present invention relates to the use of yeast cell walls or a composition comprising yeast cell walls, for the treatment of scab, in particular in fruit-trees, more particularly apple-tree scab. Another method of the invention concerns a method for the treatment of scab, in particular in fruit-trees, more particularly apple-tree, including the application of yeast cell walls or a composition comprising yeast cell walls.

Another embodiment of the invention concerns a method to induce or stimulate the immune defense mechanisms of the plant against scab, in particular in fruit-trees, including the application of yeast cell walls or a composition comprising yeast cell walls on said plant, or on part thereof.

Another embodiment of the invention concerns a method to prevent or limit the development of resistant *Venturia* strains to a fungicidal agent, wherein the treatment(s) of the plant with the said fungicidal agent used in alternation or combined with treatment(s) of said plant with yeast cell walls or a composition comprising yeast cell walls. In a particular embodiment, the method is used to limit the development of resistant *Venturia inequalis* and/or *Venturia pirina* strains.

Another particular embodiment of the invention involves the use of yeast cell walls or a composition comprising yeast cell walls to prevent or treat scab in organic or ecological farming.

Another particular embodiment of the present application concerns the use of yeast cell walls or a composition comprising yeast cell walls for the treatment of cercosporiosis, in particular in beets. Another embodiment of the invention concerns a method for the treatment of cercosporiosis, in particular in beets, including the application of yeast cell walls or a composition comprising yeast cell walls on the plant or part thereof.

Another embodiment of the invention concerns a method used to induce or stimulate the immune defense mechanisms of the plant against cercosporiosis, in particular in beets, including the application of yeast cell walls or a composition comprising yeast cell walls on the plant or part thereof.

Another embodiment of the invention involves the use of yeast cell walls or a composition comprising yeast cell walls to prevent or treat cercosporiosis in organic or ecological farming.

Other embodiment and advantages of this invention are given in the following examples, which should be considered as illustrative and not exhaustive.

EXAMPLES

Example 1

Test of the Efficiency of Compositions Using Yeast Membranes Against Apple Scab

Scab is the main disease affecting pome fruit-tree due to *Venturia inaequalis* in apple-trees.

When left untreated, scab will lead to a loss of yield and quality for up to 70% of the crop value, which leads arboriculturist to protect his orchards with 10 to 15 phytosanitary treatments throughout the season, implying important economic and environmental impacts.

The quantity of active ingredients used represent more than half of the contributions of active agrochemical ingredients globally used on apple trees, one crop using the most of phytosanitary products. Such contributions create significant quantities of residues in the soil, in the water and on the fruit itself.

The treatments currently available against scab can be categorized into four families of products:

- Products by contact do not penetrate the skin and therefore are susceptible to being washed off by the rain, are immobile and the new organs which appear after the treatment are unprotected, thereby requiring re-treating because new organs (leaves, fruit) budded or grew.
- Anilinopyrimidines partially penetrate, but do not protect organs appearing after treatment and select resistant strains of *Venturia*.
- Strobilurines, are slightly mobile into the plant, and develop resistant strains.
- Sterol biosynthesis inhibitors (SBI) have a systemic action: they are diffused in the sap. They therefore protect organs developing after treatment. These products may also develop resistance.

Limiting resistance requires the use of agrochemical products from the same family just 2 or 3 times and the alternation of families.

In these circumstances, a new composition which acts differently, producing a durable effect and which does not provide any chemical residue, would be a real advantage for arboriculturists, consumers and the environment.

This first example demonstrates the efficiency of yeast cell walls for the protection of apple-trees against scab.

Materials and Methods

The trial was conducted in a greenhouse on sowing apple-tree saplings under controlled conditions.

A population of open-pollinated seeds was put to vernalize at 4° C. in petri dishes filled with sand and damped to saturation for 90 to 120 days. The sand damp was maintained every 15 days.

From the germination of the first seeds, the seeds were sown in a plastic 40×30×15 cm seed tray, with sixty seeds per tray, of which only fifty were kept for the trial. The seeds were put in peat plugs rehydrated in a bed of potting soil (Combi-Tree B MG from the company DCM) comprising a fertiliser mix (2 kg/m$^3$ of NPK 7-7-10 and 2 kg/m$^3$ of NPK 15-8-12 slow release).

The trays were re-covered with potting soil, damped and kept at a temperature of about 10° C. for a week before being put in the ground at 18° C. Optionally, an insecticide was used during the trial.

The seedlings were treated from the 3-4 extended leaves stage with two successive treatments one week apart. The pathogen (*Venturia inaequalis*) was inoculated three days after the second treatment. Observations were made 14 and 21 days after inoculation.

The statistic framework included 3 repeats, each corresponding to a tray of 50 seedlings. The trial compared three doses of acqueous suspension (demineralized water) OY of yeast cell walls respectively adding 2.5 mg/l, 25 mg/l and 250 mg/l of cell walls to a control treated with demineralised water.

The cell walls used here are Springcell 8001 product from Biospringer SAS, (Maisons-Alfort, France), with 96% cell walls of dry matter content.

TABLE 1

| Subject | Product | Concentrations (mg/l) |
| --- | --- | --- |
| OY1 | Cell walls | 250 |
| OY2 | Cell walls | 25 |
| OY3 | Cell walls | 2.5 |
| not treated Control | Water | — |

Treatment was carried out with spraying, after shaking, with a manual 500 ml sprayer (BIRCHMEIER). Spraying was stopped up to the point of run-off. The last newly extended leaf to the day before the treatment was named 《F1》 and labeled by a fixed link to the leaf stalk.

The first newly formed or extended leaf after treatment, which had not been treated with the composition, was called 《F0》. If this leaf had formed, but not extended at the time of treatment, it was covered during spraying. The inoculation took place 3 days after treatment. F0 was at least partially extended during this period.

The inoculum *Venturia inaequalis* was prepared as follows.

Speckled leaves were collected during summer from different orchards. After 20 days drying, the leaves were put in plastic bags and frozen at −18° C. On the day of use, the leaves were placed in a 1-liter bottle comprising 200 ml of rain water, and shaken manually for 10 minutes. The suspension was cloth filtered and the obtained volume is measured.

The obtained conidia were counted under a microscope on a Bürker hematocymeter, with 2 counts of 2×144 squares, an average of which was calculated. This number of conidia was multiplied by Bürker's constant (250,000), and, to obtain a number of viable conidia, corrected by a conidia germination factor, resulting of a test carried out the day before.

On this data, the suspension of spores was diluted to obtain 150,000 viable conidia per ml. Approximately 1 liter of suspension liquid is required to inoculate 1000 plants.

The plants were inoculated by manual spraying with a suspension of 150,000 *Venturia* viable conidia per ml, and transferred into a saturated moist room for 48 hours.

The scores were assigned to F1 and F0 and indicate the sporulating surface of the leaf as a percentage of the leaf surface.

An average score per 50 plants was calculated for each repeat. The average of 3 repeats for each protocol (or method) provided an average for each protocol. Finally, the efficiency was calculated using Abott's formula:

Efficiency=[(《water》 score)−(score for the tested method)]/(《water》 score)

Results

The results are shown below in Table 2.

TABLE 2

| Observations | Sporulant Surface/leaf (%) | | Efficiency (%) | |
|---|---|---|---|---|
| Method | F1 | F0 | F1 | F0 |
| Water | 41.46 | 15.83 | 0 | 0 |
| OY1 | 17.75 | 10.39 | 57.2 | 34.4 |
| OY2 | 14.59 | 7.6 | 64.8 | 52.0 |
| OY3 | 16.9 | 8.9 | 59.2 | 43.8 |

The results show that the products of the invention are able of inducing a significant decrease in the sporulant surface, both for F1 leaves and F0 leaves forming after treatment.

In this last case, the cell walls could not penetrate the plant to be transported by the sap, therefore it is probably not a systemic action. However, this result suggests the induction of the immune defense mechanisms of the plant.

Example 2

Test of Efficiency Against Scab for Compositions Comprising Yeast Cell Walls

The test was carried out on grafted plants, in pots. Three species were used: 'Reinette des Capucins', 'Jonagold', and 'Reinette de Waleffe', grafted on M9 rootstock. The plants were grown under a plastic tunnel at different times, so that they were all at the same stage at the time of the trial: starting with Reinette de Waleffe, then 15 days later, Reinette des Capucins, then 1 week later, Jonagold.

The plants were labelled with the variety and the method of treatment received before inoculation.

The method of treatment, preparation of the inoculum, inoculation and observations are similar to those described in example 1.

The plants were treated twice, successively, 10 days apart. The day following the second treatment, the last extended leaf 《F1》 was identified.

Two days after the second treatment, the pathogen (*Venturia inaequalis*) was inoculated using a dose of $1.5 \times 10^5$ conidia/ml, directly in the moist room. Inoculation is followed by a 48 hours incubation in moist room at 18° C., then the plants remained in the boxes with a temperature of $18° \pm 2°$ C. and a relative humidity of $80 \pm 10\%$.

The study was organised as follows:

TABLE 3

| Variety | Method | Products | Concentrations (mg/l) |
|---|---|---|---|
| Jonagold | OY2 | Cell walls | 25 |
| Jonagold | BABA | β-aminobutyric acid | 2000 |
| Jonagold | Control | Water | — |
| Waleffe | OY2 | Cell walls | 25 |
| Waleffe | BABA | β-aminobutyric acid | 2000 |
| Waleffe | Control | Water | — |
| Capucins | OY2 | Cell walls | 25 |
| Capucins | BABA | β-aminobutyric acid | 2000 |
| Capucins | Control | Water | — |

The OY2 yeast cell walls correspond to an acqueous suspension at 25 mg/l of the Springcell 8001 product from Biospringer SAS, (Maisons-Alfort), France), with 96% cell walls of dry matter content.

The observations were made on the 21st day after the inoculation of the last 2 treated leaves (F2 and F1) and on the leaf newly formed after treatment (F0) for about 25 leaves per subject. Results are shown below, in table 4.

TABLE 4

| | | Sporulant surface/leaf (%) | | | Efficiency (%) | | | Leaves | All |
|---|---|---|---|---|---|---|---|---|---|
| Varieties | Method | F2 | F1 | F0 | F2 | F1 | F0 | treated | leaves |
| Capucins | water | 17.5 | 19.8 | 7.8 | — | — | — | — | — |
| Capucins | baba | 4.2 | 8.0 | 4.3 | 75.8 | 59.8 | 45.3 | 67.8 | 60.3 |
| Capucins | OY2 | 3.2 | 7.1 | 4.2 | 81.6 | 64.4 | 46.7 | 73.0 | 64.2 |
| Jonagold | water | 40.3 | 36.1 | 22.4 | — | — | — | — | — |
| Jonagold | baba | 6.0 | 17.9 | 13.9 | 85.1 | 50.5 | 38.0 | 67.8 | 57.9 |
| Jonagold | OY2 | 13.6 | 12.7 | 13.7 | 66.2 | 64.8 | 38.8 | 65.5 | 56.6 |
| Waleffe | water | 31.1 | 31.4 | 23.3 | — | — | — | — | — |
| Waleffe | baba | 18.6 | 20.4 | 20.9 | 40.3 | 35.2 | 10.3 | 37.8 | 28.6 |
| Waleffe | OY2 | 5.5 | 14.5 | 10.7 | 82.2 | 54.0 | 54.1 | 68.1 | 63.4 |
| All | water | 29.6 | 29.1 | 17.8 | — | — | — | — | — |
| All | baba | 9.6 | 15.4 | 13.0 | 67.6 | 47.1 | 27.0 | 57.4 | 47.2 |
| All | OY2 | 7.5 | 11.4 | 9.5 | 74.8 | 60.8 | 46.6 | 67.8 | 60.8 |

The mean efficiency for all varieties and all types of leaves is 60.8%, with an average of 68.8% for F2 and F1 treated leaves, and 46.6% for newly formed F0 leaves.

This efficiency was similar to, but always higher than that achieved with BABA in the same period.

An observation at 41 days after the treatment gave the following results.

TABLE 5

| Variety | Method | Sporulant surface/leaf (%) | | | | | Efficiency (%) | | |
|---|---|---|---|---|---|---|---|---|---|
| | | F2 | F1 | F0 | F-1 | F-2 | Treated leaves | New leaves | All leaves |
| Capucins | water | 90.00 | 33.55 | 36.13 | 22.57 | 4.33 | — | — | — |
| Capucins | baba | 4.00 | 10.62 | 14.07 | 9.95 | 4.00 | 88.2 | 55.5 | 77.1 |
| Capucins | OY2 | 1.80 | 7.76 | 15.69 | 11.07 | 1.92 | 92.3 | 54.5 | 79.5 |
| Jonagold | water | 50.73 | 67.69 | 64.92 | 51.54 | 22.44 | — | — | — |
| Jonagold | baba | 10.57 | 27.57 | 37.79 | 29.57 | 3.43 | 67.8 | 49.0 | 57.7 |
| Jonagold | OY2 | 20.42 | 35.71 | 52.19 | 32.56 | 12.29 | 52.6 | 30.1 | 40.5 |
| Waleffe | water | 50.00 | 54.30 | 61.35 | 56.06 | 20.18 | — | — | — |
| Waleffe | baba | 15.55 | 42.00 | 41.05 | 45.16 | 18.42 | 44.8 | 24.0 | 33.0 |
| Waleffe | OY2 | 0.50 | 15.40 | 18.59 | 17.31 | 8.07 | 84.8 | 68.0 | 75.2 |
| All | water | 63.6 | 51.8 | 54.1 | 43.4 | 15.7 | — | — | — |
| All | baba | 10.0 | 26.7 | 31.0 | 28.2 | 8.6 | 68.1 | 40.1 | 54.2 |
| All | OY2 | 7.6 | 19.6 | 28.8 | 20.3 | 7.4 | 76.4 | 50.0 | 63.4 |

At this time, new leaves had extended: F-1 and F-2, and the disease progressed by natural contamination, without any re-inoculation.

Mean efficiency represented 63.4% for all the varieties and all types of leaves. It reached an average of 76% for treated leaves, F1 and F2, and 50% for newly formed leaves: F0, F-1 and F-2.

Again, efficiency is similar to, but always higher than that for BABA in the same period.

It is important to note the long period of persistence of the fungicide effect, exceeding that of agrochemical products (between 7 to 15 days).

Example 3

Test of Protection Against Cercosporiosis in Beet

A small scale trial was carried out on cercosporiosis in beet in a greenhouse. This fungal disease is caused by *Cercospora beticola*.

Beet seeds of the FORTIS variety, known for their susceptibility to cercosporiosis, were sown in germinators. At the time of their emergence, the young seedlings were planted in pots in a greenhouse at 24° C., with a daily photoperiod of 16 hours.

The trial schedule was made up of 2 blocks (2 repeats) of 8 plants per method (or aim).

The plants were treated once, at the 4-leaves stage by spraying the leaves with a solution comprising yeast cell walls.

The solutions, named OY, were comprised of yeast cell walls (Springcell 8001 from Biospringer SAS, with 96% cell walls of dry matter content) in acqueous suspension.

The treatment consisted of spraying the obtained solutions, after shaking, using a manual sprayer. The treatment, carried out in the 4 leaves stage of beet, targeted the last two leaves fully developed and both sides of the leaf were covered up to the point of run-off.

The treated plants were kept in an enclosed space with constant humidity maintained by regular watering of the substrate.

The plants were inoculated 1 week later, at the 6 leaves stage, by spraying a conidia suspension of *C. beticola* strain 524, at 20 000 spores per ml, on both sides of the leaf, up to the point of run-off, then the plants were kept in a humid atmosphere.

The strain 524 of *Cercospora beticola* provided by "Unité de Phytopathologie de la Faculté Universitaire de Gembloux" (Belgium) was chosen for its aggressive nature.

The strain was cultivated in Petri dishes on V8 medium in individualised colonies. After 5 days of dark incubation in a growing room at a temperature of 24° C., the individualised colonies were collected in a sterile test tube containing 3 ml of sterile distilled water. Then the solution obtained was vortexed to free the conidia of the pathogen. The conidial suspension was then used to seed new Petri dishes containing freshly prepared V8 medium. The prepared cultures were incubated at 24° C. in a growing room with a photoperiod of 16 hours. After a week of incubation, the culture was collected and a conidial suspension was prepared by superficial scraping of the culture into distilled water using a scalpel blade. The number of conidia in the condial suspension was then counted using the Bürker cell chamber, and the condial suspension was adjusted to 20,000 conidia per milliliter of distilled water.

The inoculated plants were also kept in high humidity.

The extent of the symptoms was evaluated one month later using the visual scale used by The Royal Belgian Institute for the Improvement of Beet (IRBAB), which has 10 values from 0 to 9, in which 9 indicates that 100% of the leaf's surface is healthy (not covered by lesions) and 0 indicates that 0% of the leaf's surface is healthy (not covered by lesions).

The treatment is carried out using a cell walls suspension, named OY, with different concentrations, OY1, OY2, OY3, described below in Table 6.

TABLE 6

| Method | Products | Concentrations (mg/l) |
|---|---|---|
| OY1 | Cell walls | 250 |
| OY2 | Cell walls | 25 |
| OY3 | Cell walls | 2.5 |
| not treated control | Water | — |

The score assigned to each method, averaged for the two repetitions, is reported in Table 7 below.

TABLE 7

| Method | Average score | Healthy Surface in % | IRBAB criterion |
|---|---|---|---|
| not treated control | 3.94 | 85 | Insufficient |
| OY1 | 4.69 | 91 | Acceptable |
| OY2 | 6.34 | 97.5 | Very Acceptable |
| OY3 | 6.22 | 97.1 | Very Acceptable |

In this example, the cell walls enable to reach an average damage criterion of "very acceptable" from a criterion of "insufficient".

Example 4

Test of the Protection of Wheat Against *Septoria*

*Septoria* (*Septoria nodorum*, and/or *Septoria tritici*) is the main leaf disease for wheat in Europe, causing a loss of yield of up to 40% of crop. The chemical control generally consists of systematic treatment at the 2-3 nodes stage followed by a treatment at the ear emergence stage.

This trial shows that the early use of a yeast cell walls based-product can delay the appearance of the disease and replace the first chemical treatment, leading to benefits at the toxicological level for farmers and for consumers (residue) and at the environmental level.

Material and Methods

The trial was conducted in France, in an open field, on a crop of soft winter wheat of the Orvantis variety, starting on Oct. 6, 2005.

The trial was carried out according to the CEB method No M189 (Commission des Essais Biologiques, de l'Association Française pour la Protection des Plantes, Paris) and respecting Good Experimental Practice standards.

The statistical framework consisted of Fisher's randomised blocks. Each method consisted of 4 repeats, each corresponding to a basic plot of 8×2.5 m (20 m$^2$).

The trial aimed to compare the effect of yeast cell walls used in acqueous suspension (Springcell 8001 from Biospringer SAS, 96% cell walls of dry matter content), named OY, when they were used at the beginning of the treatment program against septoriosa.

The chemical reference used here is Opus (epoxyconazole 125 g/L, BASF Agricultural Products) used at 1 L/ha.

The treatment was carried out with 200 L/ha using a wheelbarrow sprayer supplied with a spray boom of 2.50 m.

Depending on the methods used, the treatment program varied as indicated in the following table. All the methods received Opus 1 L/ha 40 days after the first treatment.

TABLE 8

| Method | T at stage "tillering end/1 cm ear" | 7 days after T | 2-3 nodes Stage | 2$^{nd}$ treatment, 40 days after T |
|---|---|---|---|---|
| 1 | Dry untreated control | — | — | OPUS 1 L/ha |
| 2 | Water treated control | — | — | OPUS 1 L/ha |
| 3 | — | — | Opus 1 L/ha | OPUS 1 L/ha |
| 4 | OY at 2.5 g/ha | — | — | OPUS 1 L/ha |
| 5 | OY at 25 g/ha | — | — | OPUS 1 L/ha |
| 6 | OY at 250 g/ha | — | — | OPUS 1 L/ha |

TABLE 8-continued

| Method | T at stage "tillering end/1 cm ear" | 7 days after T | 2-3 nodes Stage | 2$^{nd}$ treatment, 40 days after T |
|---|---|---|---|---|
| 7 | OY at 50 g/ha | — | — | OPUS 1 L/ha |
| 8 | OY at 25 g/ha | OY at 25 g/ha | — | OPUS 1 L/ha |

Five observations were made in the trial period so as to evaluate the frequency and intensity of the septorosis attack:
Observation 1: Apr. 4, 2006 at T1 (BBCH 31): Stage of ear at 1 cm
Observation 2: Apr. 28, 2006 at T3 (BBCH 32): Second node stage;
Observation 3: May 15, 2006 at T4 (BBCH 39): Last leaf opened Stage.
Observation 4: May 29, 2006 at T4+15 days (BBCH 55): Mid-ear emergence stage.
Observation 5: Jun. 22, 2006 at BBCH 71: Acqueous grain stage.

Accordingly, the test schedule is the following (N=observation):

| T1 | T2 | T3 | T4 | | |
|---|---|---|---|---|---|
| Apr. 04, 2006 | Apr. 11, 2006 | Apr. 28, 2006 | May 15, 2006 | May 29, 2006 | Jun. 22, 2006 |
| BBCH 31 | BBCH 32 | BBCH 33 | BBCH 39 | BBCH 55 | BBCH 71 |
| N1 Previous septoriosa | | N2 septoriosa | N3 septoriosa | N4 septoriosa | N5 septoriosa |

For each observation, the frequency and the intensity have been determined at the 3 leaf stages (F1, F2, F3), wherein F1 refers to the last leaf to entirely open for 25 randomly chosen stalks.

The frequency corresponds to the percentage of leaves affected by septoriosa.

The intensity corresponds to the average percentage of the leaf surface affected by the disease.

The average of the 25 stalks was calculated for each repeat. The average of the 4 repeats for each method resulted in the average for each method. Finally, the efficiency was calculated using Abott's method.

Results

For the first 4 observations, the intensity of the disease remained weak (>3% in the untreated control). The efficiency of the OY method didn't appear statistically significant. On the 5$^{th}$ observation, the disease was apparent and its intensity was higher than 95% for the untreated control on the F3 leaf.

At this time, the results, the extent of the differences, and the percentages of efficiency are the following:

TABLE 9

| % of affected leaf surface | F1 Leaf = % efficiency | | | F2 Leaf = % efficiency | | | F1 + F2 Average = % efficiency | | | F3 Leaf = % efficiency | | |
|---|---|---|---|---|---|---|---|---|---|---|---|---|
| 1. Dry control | 13.5 | A | — | 45.2 | A | — | 29.35 | A | — | 96.3 | AB | — |
| 2. Water treated | 12.7 | A | — | 33.6 | B | — | 23.15 | A | — | 96.1 | AB | — |
| 3. Opus 1 L/ha | 3.4 | B | 74.80% | 13 | C | 71.20% | 8.2 | B | 73.00% | 87.5 | AB | 9.10% |
| 4. OY at 2.5 g/ha | 4.4 | B | 67.40% | 13.3 | C | 70.60% | 8.85 | B | 69.00% | 98.2 | A | -2.00% |
| 5. OY at 25 g/ha | 4.7 | B | 65.20% | 15.3 | C | 66.10% | 10 | B | 65.65% | 95.6 | AB | 0.70% |
| 6. OY at 250 g/ha | 3.7 | B | 72.60% | 13.9 | C | 69.20% | 8.8 | B | 70.90% | 84.8 | AB | 11.90% |
| 7. OY at 50 g/ha | 3.2 | B | 76.30% | 15.4 | C | 65.90% | 9.3 | B | 71.10% | 92.9 | AB | 3.50% |
| 8. OY at 25 g/ha + OY at 25 g/ha | 3.6 | B | 73.30% | 9.7 | C | 78.50% | 6.65 | B | 75.90% | 90.2 | AB | 6.30% |

The results show a significant decrease in the intensity of the disease on F1 and F2 80 days after the first treatment, and irrespective of the OY dose used. In addition, the observed average efficiencies for F1 and F2 with OY are all statistically equivalent to those observed with the Opus chemical reference.

Example 5

Test of the Protection of Protein Crop Peas Against Anthracnose

Anthracnose is one of the main leaf diseases which affects peas, and strongly decreases the grains yield. It is caused by the fungus *Ascochyta pisi*.

Material and Methods

The trial was conducted in France, in an open field, on a crop of spring protein crop peas of the Lumina variety, starting on March 22.

The trial was carried out according to CEB method No M215 (Commission des Essais Biologiques, de l'Association Française pour la Protection des Plantes, Paris) and respecting Good Experimental Practice standards.

The statistical framework consisted of Fisher's randomised blocks. Each method consisted of 4 repeats, each corresponding to a basic plot of 8×2.5 m (20 m²).

The trial included:

2 controls: 1 dry and 1 treated with water: methods 1 and 2

1 chemical reference (Dithane Neotec: Mancozeb 75%, Dow Agroscience) applied twice: method 3

3 methods with yeast cell walls used in acqueous suspension with different concentrations (Springcell 8001 from Biospringer SAS, 96% cell walls of dry matter content), named OY, methods 4-6:

Method 4: 25 g/ha

Method 5: 250 g/ha

Method 6: two treatments one week apart, at 25 g/ha then 25 g/ha

The treatment was carried out with 200 L/ha using a wheelbarrow sprayer supplied with a spray boom of 2.50 m.

The first applications were carried out on May 17, 2006 at the 7-8 leaf stage.

An artificial contamination was carried out on May 19, 2006 using mycelium and fresh spores of *Ascochyta pisi* on barley grain (20 kg of grains/1000 m²), provided by the company ARBIOTECH.

Treatment was applied as follows:

TABLE 10

| Method | T: 1ˢᵗ trifoliated leaf | 7 days after T | Flowering |
|---|---|---|---|
| 1 | Control | — | — |
| 2 | Water control | — | — |
| 3 | Dithane Neotec (2.1 kg/ha) | — | Dithane Neotec (2.1 kg/ha) |
| 4 | OY at 25 g/ha | — | — |
| 5 | OY at 250 g/ha | — | — |
| 6 | OY at 25 g/ha | OY at 25 g/ha | — |

An observation was made on Jun. 10, 2006 at the BBCH 67 stage (flowering stage), in order to evaluate the frequency and intensity of the anthracnose attack on the leaves.

The test schedule was therefore the following (N=observation):

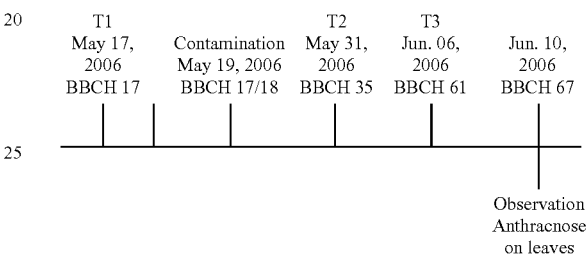

During the observation, the frequency and intensity were estimated at the 3 leaf stage (low-middle-high) for 25 stalks on a basic plot.

The frequency corresponds to the percentage of leaves affected by the disease.

The intensity corresponds to the average percentage of the affected leaf surface.

The average of the 25 stalks was calculated for each repeat. The average of the 4 repeats for each method resulted in the average for each method. Finally, the efficiency was calculated using Abott's method.

Variance was analysed, and a Neuman-Keuls test was carried out, for determining the significance of the differences between methods (same letters: identical results with risk of 5%; different letters: different results with risk of 5%).

Results

Despite artificial contamination, the anthracnose infestation remained quite weak (intensity<8% in the untreated control).

The observations, results and percentages for efficiency are shown in the following table.

TABLE 11

Intensity of anthracnose attacks on leaves and efficiency
Intensity of anthracnose attacks on leaves in terms
of % (Jun. 10, 2006 BBCH 67) and efficiency (Eff)

| N° | Treatments | Low level | | Eff | Middle level | | Eff | Low-Middle levels average | High level | |
|---|---|---|---|---|---|---|---|---|---|---|
| 1 | Dry control | 6.20 | A | — | 3.35 | A | — | — | 0.07 | B |
| 2 | Control treated with water | 5.83 | AB | — | 3.31 | A | — | — | 0.2 | B |
| 3 | Dithane Neotec (2.1 kg/ha)(twice) | 4.35 | C | 30% | 2.07 | BC | 38% | 34% | 0 | B |
| 4 | OY at 25 g/ha | 4.72 | C | 24% | 2.25 | BC | 33% | 29% | 0.38 | A |
| 5 | OY at 250 g/ha | 4.87 | CB | 21% | 1.52 | C | 54% | 38% | 0.02 | B |
| 6 | OY at 25 g/ha + OY at 25 g/ha | 4.33 | C | 30% | 2.45 | B | 27% | 29% | 0.07 | B |

The evaluation concerns the low and middle levels because the high level was not already attacked. All of the tested doses of OY proved an efficiency equivalent to that of the chemical reference.

Example 6

Test of the Protection of Vine Against Oidium (*Erysiphe Necator*)

Oidium (*Uncinula necator, Erysiphe necator*) is a vine fungal disease present in all vinyards with different intensities depending on the region and the type of vine. It is the most widely known vine disease in the world. Oidium attacks all the organs of the vine and can lead to very significant production losses.

Materials and Methods

The test was carried out in a greenhouse, in pots, on young seedlings of the Cinsaut variety. The conditions were controlled and contamination was artificial.

The seedlings were grown in a greenhouse, from one-bud cuttings, and homogenous sets were created.

The statistical framework comprised 6 repeats, each with 1 pot. The repeat having the result the farthest from the average was eliminated during the analysis.

The treatment was carried out using a spray bench with non air-assisted spray and constant pressure covering the entire plant, and plants in one same set were treated simultaneously. The bench consisted of a spray trolley, moving on a rail at a constant speed and included 5 nuzzles (2 on each side and one below the plant). The volume of treatment was equivalent to 600 liters per ha.

During the treatment, the foliar levels were marked by a coloured link fixed under the 3rd leaf fully developed in order to enable the observation of the effect of the treatment on newly formed leaves (formed after treatment).

The treatment was applied 14 or 7 days before artificial contamination. A set of plants was treated twice, at 14 days, and then 7 days before contamination.

The tested products were yeast cell walls used in acqueous suspension (Springcell 8001 from Biospringer SAS, with 96% cell walls of dry matter content), named OY.

4 doses were tested:
dose N/10: 2.5 g/ha
dose N: 25 g/ha
dose 2N: 50 g/ha
dose 10N: 250 g/ha The doses were tested according to the treatment schedule below:

TABLE 12

| | Number of days between treatment and inoculation | |
|---|---|---|
| Method | T 14 days before inoculation | T 7 days avant inoculation |
| 1 | Untreated control | — |
| 2 | OY N (25 g/ha) | — |
| 3 | — | Untreated control |
| 4 | — | OY N/10 (2.5 g/ha) |
| 5 | — | OY N (25 g/ha) |
| 6 | — | OY 2N (50 g/ha) |
| 7 | — | OY 10N (250 g/ha) |
| 8 | OY N (25 g/ha) | OY N (25 g/ha) |

The fungal material was comprised of conidia from a strain with normal susceptibility to fungicides.

All the plants in the trial were contaminated by dry sprinkling of the spores on the plants inside a plexiglass inoculation tower.

The fungal material used was comprised of spores from the *oidium* previously multiplied in a large quantity on surviving leaves or on plants. The used inoculum was 12 to 14 days old for vine *oidium*. The quality of the inoculation was verified using a Malassez cell placed at the level of the plants inside the inoculation tower. A density of 800 to 1000 spores per $cm^2$ was used.

All the plants were put into incubation after their contamination in a climatised room with a temperature of 21±2° C. with 14 hours of light by day. Each trial condition was entirely isolated from the others in mini enclosures.

The plants remained in this condition for 14 days. At the end of this period, the fungal damage was observed.

Observations

The leaves at the higher foliar levels F2, F1 and F0 (level formed after treatment) were assigned a score. Each leaf was scored by a visual observation. The frequency (percentage of leaves affected by the disease) was not indicated because all leaves were affected. The intensity (average percentage of leaf surface affected) was evaluated on a scale of 0 to 100.

Efficiency was calculated, using Abott's method, on the basis of average intensities, and variance was analysed. A Neuman-Keuls test allowed an evaluation of the significance of differences between the methods (same letters: identical results with risk of 5%; different letters: different results with risk of 5%).

Results

Table 13: Rate of damage on plants treated on different dates (14 and 7 days before inoculation with *E. necator*) with the solution named OY (Springcell 8001 from Biospringer SAS). Observation on sensitive leaves F2, F1, F0:

| Method | Days between treatment and infection | Intensity of attack (%) | | Effeciency |
|---|---|---|---|---|
| Control | 14 days | 47.4 | AB | — |
| N | 14 days | 48.0 | AB | 0 |
| Control | 7 days | 61.3 | A | — |
| N/10 | 7 days | 40.1 | AB | 34.6 |
| N | 7 days | 32.7 | ABC | 46.7 |
| 2N | 7 days | 23.3 | BC | 62 |
| 10N | 7 days | 21.3 | BC | 65.3 |
| N + N | 14 days + 7 days | 14.1 | C | 70.3 |

A single application 14 days before inoculation didn't protect the leaves.

However, the applications carried out 7 days before contamination had a protective effect against *oidium*. Stronger doses (2N at 50 g/ha and 10N at 250 g/ha) had a stronger effect.

An application of 25 g/ha (dose N) 14 days before inoculation, followed by an identical application, 7 days before inoculation, gave excellent results.

Example 7

Test of Protection of Vines Against Downy Mildew (*Plasmopara viticola*)

Mildew is from the fungus (*Plasmopara viticola*). Present at diverse degrees in most vinyards in the world, it harms the yield and the quality of the crop, up to the point of complete destruction if it is not treated.

Material and Methods

The trials were carried out in a greenhouse, in pots on young seedlings of the Cabernet-Sauvignon variety. The trial conditions were controlled and the contamination was artificial.

The plants were produced in a greenhouse from one-bud cuttings and homogenous sets were created.

The statistical framework included 6 repeats, each of 1 pot. The repeat having the result the farthest from the average was eliminated during the analysis.

The treatment was carried out using a spray bench with non air-assisted spray and constant pressure covering the entire plant, and plants in one same set were treated simultaneously. The bench consisted of a spray trolley, moving on a rail at a constant speed and included 5 nuzzles (2 on each side and one below the plant). The volume of treatment was equivalent to 600 liters per ha.

During the treatment, the foliar levels were marked by a coloured link fixed under the 3rd leaf fully developed in order to enable the observation of the effect of the treatment on newly formed leaves (formed after treatment).

The treatment was applied 14 or 7 days before artificial contamination. A set of plants was treated twice, at 14 days, and then 7 days before contamination.

The tested products were yeast cell walls used in acqueous suspension (Springcell 8001 from Biospringer SAS, with 96% cell walls of dry matter content), named OY.

4 doses were tested:
dose N/10: 2.5 g/ha
dose N: 25 g/ha
dose 2N: 50 g/ha
dose 10N: 250 g/ha The doses were tested according to the treatment schedule below:

TABLE 14

| | Number of days between treatment and inoculation | |
|---|---|---|
| Method | T 14 days before inoculation | T 7 days before inoculation |
| 1 | — | — |
| 2 | — | OY N/10 (2.5 g/ha) |
| 3 | — | OY N (25 g/ha) |
| 4 | — | OY 10N (250 g/ha) |
| 5 | — | OY 2N (50 g/ha) |
| 6 | OY N (25 g/ha) | OY N (25 g/ha) |
| 7 | OY N (25 g/ha) | — |

The plants were inoculated simultaneously by spraying a suspension of sporocysts from the strain *Plasmopara viticola* which is normally sensitive to fungicides.

The sporocyst suspension was prepared just before contamination. The sporulations of the fungus were collected by washing infected leaves with permuted water. Titration was carried out using a Malassez cell. The used concentration was 50 000 spores/ml.

10 ml of the spore suspension was sprayed on the plant, on the lower surface of the leaf. Each plant was individually contaminated, at all levels of the existing leaves.

The plants were then regrouped by method and isolated in separate enclosures.

The plants were kept under fogging to favour the development of the disease, at a temperature of 21° C., and with 14 hours of light per day, for 8 days. Observations were carried out at the end of this period.

Observations

Each leaf was observed visually. The frequency (percentage of leaves affected by the disease) was not scored as all leaves were affected.

The intensity (average percentage of leaf surface affected) was evaluated on a scale of 0 to 100.

Efficiency was calculated, using Abott's method, on the basis of average intensity.

Results

The results for intensity and efficiency were regrouped as treated leaves or as newly formed and therefore untreated leaves.

TABLE 15

| | | Treated leaves | | Newly formed leaves | |
|---|---|---|---|---|---|
| Method | Number of days between treatment and infection | Intensity of the attack (%) | Efficiency (%) | Intensity of the attack (%) | Efficiency (%) |
| Control | 14 days | 68.0 | — | 67.3 | — |
| N | 14 days | 31.3 | 54 | 45.0 | 33.1 |
| Control | 7 days | 82.0 | — | 48.1 | — |
| N/10 | 7 days | 62.7 | 23.5 | 40.5 | 15.8 |
| N | 7 days | 54.7 | 33.3 | 23.6 | 50.9 |
| 2N | 7 days | 50.0 | 39 | 23.5 | 51.1 |
| 10N | 7 days | 42.7 | 47.9 | 28.0 | 41.8 |
| N + N | 14 days + 7 days | 25.4 | 62.6 | 40.7 | 39.5 |

All the tested doses of the cell walls had an effect on mildew of the treated or newly formed leaves, irrespective of the period between treatment and contamination. Efficiency tended to increase with the dose.

Example 8

Open Field Test for the Protection of Vines Against Mildew

Material and Methods

The test was carried out in France, close to Bordeaux, in an open field, on vines of the Cabernet-Sauvignon variety. The test was carried out respecting Good Experimental Practice standards.

Trial plots were installed and the first applications carried out on May 25, 2006 at BBCH 55 stage. The statistical framework consisted of Fisher's randomised blocks. Each method consisted of 4 repeats, each corresponding to a basic plot of 10 vine stocks. The trial included:

1 untreated control;
2 methods using OY in an acqueous suspension (Springcell 8001 from Biospringer SAS, 96% cell walls of dry matter content).

The treatment was carried out with 1000 L/ha using a Solo mist blower.

The treatment was carried out on a weekly basis from 25 May (BBCH 55 stage)

TABLE 16

| Method | Weekly treatment |
|---|---|
| 1 | Untreated |
| 2 | OY 4N (100 g/ha) |
| 3 | OY 10N (250 g/ha) |

Observations were carried out before application. Observation was carried out on Aug. 18, 2006 due to the late appearance of the disease.

The frequency and intensity on the leaves were estimated for 50 randomly taken leaves, per basic plot, i.e. 5 leaves from each vine stalk.

The frequency corresponds to the percentage of leaves affected by the disease. The intensity corresponds to the average percentage of affected leaf surface.

The average of the 50 leaves was calculated for each repeat. The average of the 4 repeats for reach method leads to a method average.

Finally, efficiency was calculated, using Abott's method, on the basis of the average intensities.

Results

The results and percentages of efficiency are the following.

TABLE 17

Mildew scores for leaves on August 18 - BBCH 83

| Method | Treatment | Frequency/ leaves (%) | Intensity/ leaves (%) | Efficiency (%) |
|---|---|---|---|---|
| 1 | Untreated control | 48.8 | 13.3 | — |
| 2 | OY 4N (100 g/ha) | 53.0 | 9.9 | 25.56 |
| 3 | OY10N (250 g/ha) | 45.5 | 5.5 | 58.64 |

The efficiency of the product was observed at the 2 tested doses, 100 and 250 g/ha.

The invention claimed is:

1. A method for the treatment or protection of a plant against disease caused by pathogenic agents comprising the application of a whole yeast cell walls as an active ingredient on the plant or a part thereof.

2. A method for inducing or stimulating the immune defense of a plant comprising the application of a whole yeast cell walls as an active ingredient on the plant or a part thereof.

3. The method according to claim 1 or 2, wherein the plant is selected from the group consisting of graminaceae and dicotyledons, annual, biennial and perennial plants, vegetables, cereals, wheat, barley, rice, corn, sorghum, millet, oil seed, protein crop, potatoes, beets, sugar cane, tobacco, ligneous plants, trees, fruit-trees, vines, and ornamental plants.

4. The method according to claim 3, wherein the plant is a fruit-tree.

5. A method according to claim 1 or 2, wherein the pathogenic agent is a fungus, virus, bacteria, mycoplasm, spiroplams or viroid.

6. The method according to claim 5, wherein the pathogenic agent is selected from the group consisting of the species of fungi *Alternaria* spp, *Ascochyta* spp, *Botrytis* spp, *Bremia* spp, *Cercospora* spp, *Cladosporium* spp, *Colletotrichum* spp, *Erysiphe* spp, *Fusarium* spp, *Gloeosporium* spp, *Guignardia* spp, *Helminthosporium* spp, *Marssonina* spp, *Monilia* spp, *Mycosphaerella* spp, *Penicilium* spp, *Peronospora* spp, *Pezicula* spp, *Phragmidium* spp, *Phytophtora* spp, *Plasmopara* spp, *Podosphaera* spp, *Pseudocercosporella* spp, *Pseudoperonospora* spp, *Pseudopeziza* spp, *Puccinia* spp, *Pythium* spp, *Ramularia* spp, *Rhizoctonia* spp, *Rhizopus* spp, *Rynchosporium* spp, *Sclerotinia* spp, *Septoria* spp, *Sphaerotheca* spp, *Taphrina* spp, *Uncinula* spp, *Ustilago* spp, and *Venturia* spp.

7. The method according to claim 1 or 2, wherein the yeast cell walls belong to a *Saccharomyces* species.

8. The method according to claim 1 or 2, wherein the yeast cell walls are obtained by;
the lysis of yeast cells, leading to the formation of a soluble fraction and an insoluble fraction,
separating the soluble and insoluble fractions, and
collecting the insoluble fraction, wherein the insoluble fraction is whole yeast cell walls.

9. The method according to claim 8, wherein the insoluble fraction (whole yeast cell walls) is separated by centrifugation.

10. The method according to claim 1 or 2, wherein the yeast cell walls are further combined with one or several formulation agents.

11. The method according to claim 1 or 2, wherein the yeast cell walls are further combined with a fungicidal, antiviral or antibacterial agent.

12. The method according to claim 1 or 2, wherein the yeast cell walls are further combined with one or more immune defense elicitors of a.

13. The method according to claim 1 or 2, wherein the yeast cell walls are in a concentrated phytosanitary composition, in dry or liquid form.

14. The method according to claim 1 or 2, wherein the yeast cell walls are in a ready-to-use composition.

15. The method according to claim 1 or 2, wherein the yeast cell walls administered by spraying the leaves or soil.

16. The method according to claim 1 or 2, wherein the yeast cell walls are administered to the roots.

17. The method according to claim 1 or 2, wherein the yeast cell walls are administered to the whole plant or part thereof, leaves, stem, flowers, fruits, trunk or roots.

18. The method according to claim 1 or 2, wherein the yeast cell walls are applied or employed in an efficient dose higher than 1 mg/l of yeast cell walls when yeast cell walls are applied by spraying up to the point of run-off, or higher than 1 g/ha when spraying using a small amount of water.

19. The method according to claim 18, wherein the yeast cell walls are applied or employed in an efficient dose from 1 to 250 mg/l of yeast cell walls, or from 1 to 250 g/ha when spraying with a small amount of water.

20. The method according to claim 1 or 2, wherein the yeast cell walls are used in alternation and/or in combination with an antifungal treatment or an antibacterial treatment.

21. The method according to claim 4, wherein the fruit tree is a pome fruit tree.

22. The method according to claim 21, wherein the pome fruit tree is selected from the group consisting of apple trees, pear trees and citrus trees.

23. The method according to claim 5, wherein the pathogenic agent is selected from the group consisting of the species of fungi *A. solani, A. fabae, A. pinodella, B. cinerea, B. lactucae, C. beticola, C. allii-cepae, C. graminicola, E. graminis, F. oxysporum, F. roseum, G. fructigenum, G. bidwellii, H. tritici-repentis, M. rosae, M. fructigena, M. brassicicola, P. expansum, P. digitatum, P. parasitica, P. rubiidaei, P. infestans, P. viticola, P. leucotricha, P. brassicae, P. cubensis, P. medicaginis, P. graminis, R betae, R. solani, R. nigricans, R. secalis, S. sclerotiorum, S. nodorum, S. tritici, S. macularis, T pruni, U. necator, U. tritici,* and *V. inaequalis.*

24. The method according to claim 7, wherein the *Saccharomyces* species, is *S. cerevisiae*.

25. The method according to claim 12, wherein the one or more immune defense elicitors of a plant are selected from the group consisting of β-aminbutyric acid, 2,6-dichloroisonicotinc acid, acibenzolar-s-methyl and algae extracts.

26. The method according to claim 18, wherein the yeast cell walls are applied or employed in an amount from 1 to 1000 mg/l of yeast cell walls when yeast cell walls applied by spraying up to the point of run-off, or from 1 to 1000 g/ha.

27. The method according to claim 19, wherein the yeast cell walls are applied or employed in an amount from 25 mg to 250 mg/l when yeast cell walls are applied by spraying up to the point of run-off, or from 25 to 250 g/ha.

* * * * *